(12) United States Patent
Glaser

(10) Patent No.: US 7,404,974 B2
(45) Date of Patent: Jul. 29, 2008

(54) MEDICAMENT, IN PARTICULAR FOR THE TREATMENT OF DIABETES MELLITUS TYPE 2

(75) Inventor: Roland Glaser, Sta. Maria E 7-35 y Reina Victoria, Quito (EC)

(73) Assignees: Roland Glaser, Quito (EC); Christian Huber, Munich (DE)

( * ) Notice: Subject to any disclaimer, the term of this patent is extended or adjusted under 35 U.S.C. 154(b) by 65 days.

(21) Appl. No.: 10/561,239

(22) PCT Filed: Jun. 25, 2004

(86) PCT No.: PCT/EP2004/006917

§ 371 (c)(1),
(2), (4) Date: Dec. 19, 2005

(87) PCT Pub. No.: WO2004/112904

PCT Pub. Date: Dec. 29, 2004

(65) Prior Publication Data

US 2007/0059384 A1 Mar. 15, 2007

(30) Foreign Application Priority Data

Jun. 25, 2003 (DE) ................................ 103 28 597

(51) Int. Cl.
*A61K 36/00* (2006.01)
(52) U.S. Cl. .................................................... 424/773
(58) Field of Classification Search ........................ None
See application file for complete search history.

(56) References Cited

OTHER PUBLICATIONS

Batatinha et al., Toxic effects of Mascagnia rigida in laboratory animals, 1988, Vet. Hum. Toxicol., 30(3): 259.*
Anderson, Memoris of the new york botanical garden, 1981, vol. 32, pp. 224-225.*
Anonymous: "Ayahuasca recipes" Internet Article, "Online", Apr. 27, 2003, www.biopark.org/ayarecipe.html., "A working list of confirmed ayahuasca admixture plants," Malphghiaceae, Mascagnia psylophylla.
Database Biosis, "Online", Biosciences Information Service, Apr. 1998, Hubinger et al., "Experimental poisoning in rabbits by Mascagnia sp (Malpighiaceae) collected in the State of Santa Catarina, southern Brazil".
Artschwager, "Healing with Plants in the American and Mexican West," Internet Article, "Online " 1996, www.uapress.arizona.edu/books/bid977.

* cited by examiner

*Primary Examiner*—Susan Hoffman
*Assistant Examiner*—Catheryne Chen
(74) *Attorney, Agent, or Firm*—Rothwell, Figg, Ernst & Manbeck, P.C.

(57) ABSTRACT

The present invention relates to a medicament, comprising plant material of *Mascagnia eggersiana*, subspecies, ecotypes or a combination thereof, or, respectively, comprising active compounds obtainable therefrom. The medicament is in particular suitable for the prophylaxis or treatment of diabetes mellitus type 2, and for improving the blood flow, in particular in peripheral blood vessels. Further subject matter of the invention is the use of said plant material or of said active compounds obtainable therefrom for the prophylaxis or treatment of diabetes mellitus type 2, or for improving the blood flow, in particular in peripheral blood vessels, respectively, as well as for the preparation of respective medicaments. Further subject matter of the invention are respective therapeutic processes.

15 Claims, No Drawings

MEDICAMENT, IN PARTICULAR FOR THE TREATMENT OF DIABETES MELLITUS TYPE 2

CROSS REFERENCE TO RELATED APPLICATION

This application is a 35 USC §371 National Phase Entry Application from PCT/EP2004/006917, filed Jun. 25, 2004, and designating the United States.

The present invention relates to a medicament comprising material or active agents, respectively, of plants. In particular, the present invention relates to a medicament for the treatment and/or prophylaxis of diabetes mellitus type 2, and to a medicament for improving the blood flow, in particular of peripheral blood vessels.

Diabetes mellitus type 2, also referred to as adult-onset diabetes, is a disorder of the carbohydrate metabolism with an onset typically at an age older than 30 years. It has been observed in the recent past, however, that this disorder increasingly also affects young humans having overweight. According to WHO estimates more than 143 million humans suffered from diabetes mellitus type 2 in 1998, and the number of affected humans is expected to increase to 300 million by the year 2025.

In contrast to diabetes mellitus type 1 which is a disorder resulting strictly from a lack of insuline, the development of diabetes mellitus type 2 does not result from a lack of insuline. Diabetes mellitus type 2 rather results from a reduced action of insuline, wherein the body cannot respond appropriately to this hormone. It is believed that the causes therefore are associated with a defect of body cells to incorporate insuline in sufficient quantity and/or a defect of the Langerhans cells of the pancreas to provide insuline in a form which meets the demand. This condition is generally referred to as insuline resistance. In the initial stage of the disorder, the body attempts to restore the equilibrium by an increased insuline production, which results in an increasingly higher production of insuline and may result in an exhaustion of the pancreas in later stages of the disorder.

Diabetes mellitus is classified into type 2A, associated with normal body weight, type 2B, associated with overweight, and type 2C which is induced by medicaments. In the industrialized countries diabetes type 2B which is associated with overweight is the most prominent type, for which reason this disorder is often considered a civilization disease.

The treatment of diabetes mellitus type 2 comprises primarily a reduction of the body weight on basis of a balanced diet in combination with controlled physical workouts. If these general measures do not result in the desired success, treatment with medicaments may become required.

The following groups of medicaments for the treatment of diabetes mellitus type 2 may be distinguished:
resorption delaying agents such as acarbose delay the absorption of glucose from the intestine and thus avoid peaks of the blood glucose level,
biguanides such as metformin inhibit gluconeogenesis and reduce insuline resistance,
sulfonyl ureas such as glibenclamide induce insuline production,
insuline sensitizers such as glitazone improve the insuline sensitivity of the cells, and
insuline and insuline analogs.

There is a continuing need, however, for novel medicaments for the treatment and/or prophylaxis of diabetes mellitus type 2. Such medicaments should be highly tolerable for the patients and exhibit as few damaging side effects as possible.

Accordingly, it is a subject matter of the present invention to provide a medicament for the treatment and/or prophylaxis of diabetes mellitus type 2.

Surprisingly, it now has been found that

*Mascagnia eggersiana* (Nied.) W. R. Anderson (in the following abbreviated as *Mascagnia eggersiana*) is suitable for the for the treatment of diabetes mellitus type 2.

*Mascagnia eggersiana* is a plant of the plant family *Malphigiaceae*, its existence has been reliably established for the Napo province in Ecuador, and it naturalls grows in an area which at least extends along the Eastern slopes of the Andes of Ecuador in an altitude of 500-600 m and less. No information regarding a further extension of its natural distribution area is presently available. As used in the present application, the term *Mascagnia eggersiana* comprises the subject species as well as ecotypes and subspecies thereof. Die terms "ecotype" and "subspecies" are used herein in the usual meaning.

A reference sample of *Mascagnia eggersiana* may be found in Germany at least in the national botanical collection (Botanische Staatssammlung) of Munich, abroad of Europe reference samples may be found at least in several botanical institutes within the USA. A specimen of *Mascagnia eggersiana* is presently cultured at the botanical institute of the University of Munich.

Accordingly, one subject of the present invention is a medicament, comprising plant material of *Mascagnia eggersiana*, subspecies, ecotypes or a combination thereof. A further subject of the present invention is a medicament, comprising plant active compounds, characterized in that the plant active compounds are obtainable from plants, selected from *Mascagnia eggersiana*, subspecies, ecotypes or a combination thereof.

According to a first aspect, the medicament of the invention as described above is a medicament for the prophylaxis or treatment of diabetes mellitus type 2. It has been determined during the experimental studies, however, that the patients participating in the studies experienced a "tingling" in the peripheral limbs such as toes and finger tips, and that the blood flow startet to improve. According to a second aspect the medicament of the invention is thus a medicament for improving the blood flow, in particular in peripheral blood vessels.

According to a preferred embodiment of the medicament comprising active compounds, the active compounds are obtained from *Mascagnia eggersiana*, subspecies, ecotypes or a combination thereof.

The previous studies werde predominantly made with young plants which were reproduced from cuttings and had the morphology of a bush having a diameter of from about 0.3 to 1.2 m. In later development stages *Mascagnia eggersiana* forms shoots having a height of several meters. According to a particular embodiment, the medicament thus comprises plant material or active compounds, respectively, from *Mascagnia eggersiana*, subspecies, ecotypes or a combination thereof, derived from young plants, for example from young plants having a height above the ground of less than 1.2 m, in particular having a height above the ground of from 0.3 to 1 m.

According to a particular embodiment, the plant material is derived from the root, or the active compounds, respectively, are obtained from the root. Other parts of the plant, such as the plant body or the leaves are suitable as well, however.

For example, the root as such may be ingested, i.e. taken orally, or it may be dried and be taken orally, suitably after grinding to a powder. For the drying of the roots, simple air-drying at ambient temperature is sufficient and suitable. Before ingestion or grinding, respectively, woody components are suitably removed, such as the woody stalk of the root.

A still further subject of the present invention is the use of plant material of *Mascagnia eggersiana*, subspecies, ecotypes or a combination thereof for the preparation of a medicament for the prophylaxis or treatment of diabetes mellitus type 2 or, respectively, for the preparation of a medicament for improving the blood flow, in particular in peripheral blood vessels.

A still further subject of the present invention is the use of plant material of *Mascagnia eggersiana*, subspecies, ecotypes or a combination thereof for the prophylaxis or treatment of diabetes mellitus type 2 or, respectively, for improving the blood flow, in particular in peripheral blood vessels.

A still further subject of the present invention is the use of plant active compounds, obtainable from plants, selected from *Mascagnia eggersiana*, subspecies, ecotypes or a combination thereof, for the preparation of a medicament for the prophylaxis or treatment of diabetes mellitus type 2 or, respectively, for the preparation of a medicament for improving the blood flow, in particular in peripheral blood vessels.

A still further subject of the present invention is the use of plant active compounds, obtainable from plants, selected from *Mascagnia eggersiana*, subspecies, ecotypes or a combination thereof, for the prophylaxis or treatment of diabetes mellitus type 2 or, respectively, for improving the blood flow, in particular in peripheral blood vessels.

Particular and preferred embodiments of the uses according to the invention are as described above in the context of the medicaments according to the invention.

A still further subject of the present invention is a process for the prophylaxis or treatment of diabetes mellitus type 2, comprising administering of plant material from *Mascagnia eggersiana*, subspecies, ecotypes or a combination thereof or, respectively, administering of plant active compounds obtainable thereof, to an individual.

A still further subject of the present invention is process for improving the blood flow, in particular in peripheral blood vessels, comprising administering of plant material from *Mascagnia eggersiana*, subspecies, ecotypes or a combination thereof or, respectively, administering of plant active compounds obtainable thereof, to an individual.

According to a particular embodiment of the respective processes according to the invention, the active compounds are obtained from *Mascagnia eggersiana*, subspecies, ecotypes or a combination thereof.

The dose to be administered in the processes according to the invention depends on the severity of the disorder, and the age, weight and general physical condition of the patient. In the previous studies the daily dose used was three level spoonful, which were administered at morning, at noon and in the evening. No side effects were observed when using this dose. According to a particular embodiment, the total daily dosis is 1-100 g, based on dried plant material, in particular 10-80 g, for example 25-50 g.

The invention claimed is:

1. A medicament, comprising ground plant material of *Mascagnia eggersiana*, subspecies, ecotypes or a combination thereof.

2. The medicament of claim 1, for the treatment of diabetes mellitus type 2.

3. The medicament of claim 1, for improving blood flow.

4. The medicament of claim 1, comprising material from plants having a height of less than 1.2 meters.

5. The medicament of claim 1, characterized in that said plant material is derived from the root.

6. A process for the treatment of diabetes mellitus type 2, comprising administering an effective amount of ground plant material of *Mascagnia eggersiana*, subspecies, ecotypes or a combination thereof, to an individual in need of such treatment.

7. The process of claim 6, wherein said ground plant material is derived from plants having a height of less than 1.2 meters.

8. The process of claim 6, wherein said plant material is derived from the root.

9. The process of claim 6, wherein the total daily dose is 1-100 g, based on dried ground plant material.

10. A process for improving blood flow, comprising administering an effective amount of ground plant material from *Mascagnia eggersiana*, subspecies, ecotypes or a combination thereof, to an individual in need of such improvement.

11. The process of claim 10, wherein said ground plant material is derived from plants having a height of less than 1.2 meters.

12. The process of claim 10, wherein said plant material is derived from the root.

13. The process of claim 10, wherein the total daily dose is 1-100 g, based on dried ground plant material.

14. The medicament of claim 3, wherein the improving blood flow is in peripheral blood vessels.

15. The process of claim 10, wherein the improving blood flow is in peripheral blood vessels.

* * * * *